United States Patent [19]

Bloxom, Jr.

[11] Patent Number: 4,692,158
[45] Date of Patent: Sep. 8, 1987

[54] PORTABLE IRRIGATION ASSEMBLY

[76] Inventor: Ingrid B. Bloxom, Jr., P.O. Box 357, Wicomico, Va. 23184

[21] Appl. No.: 825,506

[22] Filed: Feb. 3, 1986

Related U.S. Application Data

[63] Continuation-in-part of Ser. No. 719,175, Apr. 2, 1985, Pat. No. 4,617,011.

[51] Int. Cl.$^4$ .............................................. A61M 5/00
[52] U.S. Cl. ........................................ 604/260; 604/54
[58] Field of Search .................... 604/260, 48, 54, 55, 604/257, 262, 246; 222/41, 51

[56] References Cited

U.S. PATENT DOCUMENTS 4,014,332  3/1977  Sneider ................................. 604/262
4,384,581  5/1983  Conway ........................... 604/260 X

FOREIGN PATENT DOCUMENTS 0000036  of 1877  Fed. Rep. of Germany .

Primary Examiner—Stephen C. Pellegrino
Attorney, Agent, or Firm—John Cyril Malloy

[57] ABSTRACT

A portable, disposable irrigation assembly of the type used to flush fecal matter from the intestine when normal bodily functions are not sufficient to accomplish evacuation of the intestine. Irrigation of the intestine by irrigating fluid is provided by directing the irrigating fluid from a storage reservoir through an elongated conduit into the intestine by an introduction cone or like structure. The creation of peristaltic action is indicative of sufficient quantity of irrigating fluid being introduced wherein such peristaltic action is sufficient to accomplish evacuation of the fecal matter. An indicator element is disposed within the flow path and along a path of liquid flow of the irrigating fluid and is specifically structured to flow in the same direction as the irrigating fluid from the reservoir to the intestine and in a reverse direction, from the intestine back through the conduit when peristaltic action is sufficient. Flow of irrigating liquid is stopped upon a sufficient indication of reverse flow through movement of the indicator element.

11 Claims, 6 Drawing Figures

U.S. Patent    Sep. 8, 1987    4,692,158
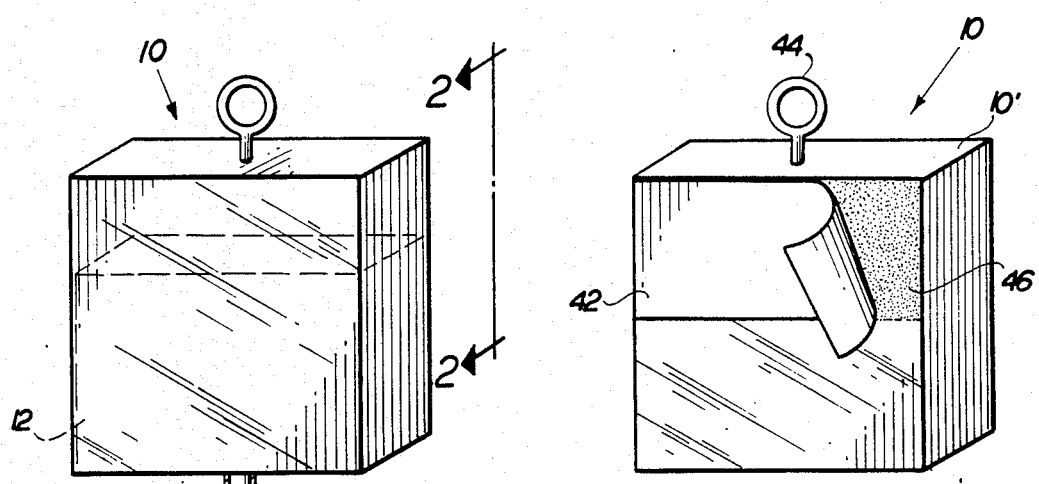
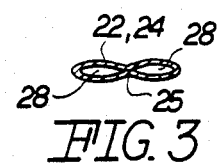
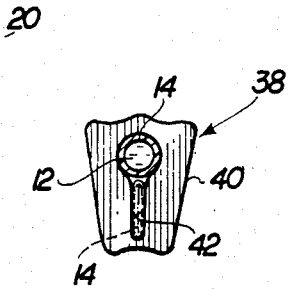
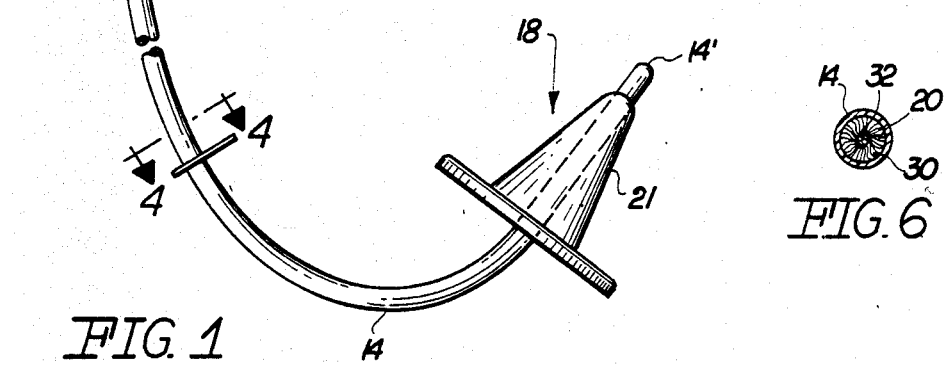

PORTABLE IRRIGATION ASSEMBLY

BACKGROUND OF THE INVENTION

This is a continuation-in-part application of copending U.S. patent application Ser. No. 719,175, filed Apr. 2, 1985 now U.S. Pat. No. 4,617,011.

1. Field of the Invention

An intestinal irrigation and flushing system capable of determining sufficient quantity of irrigating fluid being supplied to the intestine through the detection of peristaltic action in the intestine which causes reverse liquid flow from a stoma or rectum through a flow channel carrying irrigating fluid. An indicator element travels with and in the direction of liquid passing through the flow channel which directs the irrigating fluid between a reservoir and the intestine to be flushed such that reverse flow of the irrigating liquid caused by peristaltic action, forces the indicator element to an extreme position within the flow channel thereby indicating sufficient peristaltic action has been established and the ceasing of irrigating liquid.

2. Description of the Prior Art

Colonic irrigation is a well known medical treatment and is utilized not only in the case of conventional enemas through the anus end of the rectum, but also in the case of irrigation through surgically provided openings into other parts of the colon. Such is the case in colostomy patients. In providing such irrigation and flushing treatment, for the purpose of evacuating fecal matter, the decree of discomfort and length of ordeal is significant.

Of varying and particular cases, the treatment has been found to be particularly disagreeable for those requiring irrigation of the intestine directly into the colon through a surgically provided stoma. Such stomas are formed from the end of a shortened colon after the end has been secured to an opening in the stomach wall and anchored to the outer skin for clear access thereto.

Equipment to introduce irrigation liquid into the colon of the colostomy patient is disclosed, for example, in U.S. Pat. No. 3,830,235 to Marson. Such equipment conventionally includes a supply bag for irrigating liquid, a flexible tube or conduit to convey liquid from the bag to the stoma by means of a stoma cone through which liquid is introduced into the colon, a clip or like structure to shut off the flow through the tube, and a discharge device to catch the backflow or evacuated fecal matter when the cone is removed from the stoma. Typically, the irrigation liquid is water or water with a softening agent. Such agents are disclosed for example in U.S. Pat. No. 4,052,986 to Scasie. Other U.S. patents of interest include Dierker, U.S. Pat. No. 2,024,967; Stack, U.S. Pat. No. 2,832,341; Pittam, U.S. Pat. No. 1,758,332; and Coombs, U.S. Pat. No. 2,257,072.

While prior equipment and systems, of the type described above, are operable to accomplish flushing and evacuation of the colon, prior art systems of this type are generally recognized, especially by patients having to undergo treatment, as having certain disadvantages. Such disadvantages relate directly to the degree of discomfort and length of time to accomplish treatment. More specifically, there is a need in the prior art to provide means to detect or determine the minimal amount of irrigating fluid to be applied to the colon, through either the stoma or rectum, to accomplish the need of evacuation of the fecal matter. In order to determine the minimal amount of fluid to be administered to the intestine, a preferred system would be structured to detect the build-up of peristaltic action in the intestine in response to injection of irrigating liquid. Such supply of irrigating liquid would be terminated when there is an indication of sufficient peristaltic action in the intestine to provide the desired evacuation without the aid of additional irrigating liquid. Such prompt termination has the further and important advantage of preventing an excessively large injection of liquid from causing a supression of the peristaltic action originally initiated by a smaller amount of irrigation liquid initially injected.

When the introduction of irrigating liquid is made in accordance with the preferred intestinal irrigation system, injection of about one-half pint or less is normally sufficient. Further, under most circumstances it is best not to exceed one pint before terminating further introduction of irrigating liquid and applying a laxative preliminarily to renewing the introduction of irrigating fluid the next day. Conventional irrigation systems, known in the prior art, frequently call for injection of one or two quarts of liquid. Such excessive amounts of irrigation liquid being injected into the intestine serves to suppress the peristaltic action and thereby tends to prolong the period of evacuation afterwards as well as lengthening the procedure time required to administer. All of the above greatly adds to the discomfort of the patient and in some cases can be extremely dangerous. Severe cramps, nausea, rupture of the intestine or water intoxication may occur.

Accordingly, a preferred intestinal irrigation system is of the type disclosed and cliamed in my U.S. Pat. No. 4,518,382. However, further improvements in such an irrigation system can be accomplished, as disclosed herein in greater detail, by providing a portable system which may be carried with the user of such an irrigation system such as when traveling or on a day-to-day basis for example to be used at work if such is deemed necessary.

Accordingly, there is an additional need in the prior art for a portable irrigation assembly capable of being packaged or stored in a small amount of space and being made of lightweight material so as to be easily carried with the user on his person.

SUMMARY OF THE INVENTION

The present invention is directed towards a system for colonic and other intestinal irrigation wherein specific structural provision is made to visually indicate, to the user, the existence of peristaltic action in the intestine of sufficient degree to accomplish evacuation of fecal matter therefrom. Such indication of sufficient peristaltic action in turn serves as a signal to stop flow of irrigating fluid into the intestine.

The system of the present invention incorporates a supply of irrigating fluid such as water which may include additional softening agents for the purpose of allowing passage of fecal matter from the intestines being irrigating with a minimum amount of resistance. In accordance with the present invention, a confined path of fluid flow in the form of a conduit or flexible tubing extends in a depending fashion from a fluid supply or reservoir to an introduction means in the form of a plastic or like material stoma or rectum cone. The cone is secured to the distal end of the conduit and positioned in direct communication with the interior of the intestine through the rectum or surgically formed stoma. It should be emphasized that reference to the details of the present invention are described with irrigating liquid being applied to the stoma or the rectum. The system of the present invention is applicable to the evacuation of fecal matter from the intestine through either a stoma or the rectum depending upon the particular condition of the patient. Accordingly, reference to either a stoma or the rectum is not intended to limit the application of the system of the present invention.

A flow channel is mounted along the path of fluid flow so as to define a part thereof. The flow channel comprises a tubular section structured to allow passage of irrigating liquid therethrough in either direction relative to the longitudinal axis of the conduit and flow channel. The flow channel does not necessarily have to be maintained in a horizontal orientation but rather, may be a part of the conduit which depends in a substantially vertical orientation as the conduit defining the path of fluid flow extends from the supply reservoir of irrigating fluid to the stoma cone for introduction into the intestine.

An important feature of the present invention is the provision of an indicator element disposed on the interior of the flow channel and structured to pass along its length in the direction of fluid flow of the irrigating liquid. To accomplish this, the subject indicator element is specifically structured to be suspended in the irrigating liquid in the flow channel and accordingly has a specific gravity minimally greater than the specific gravity of the irrigating liquid passing through th flow channel. This allows the above set forth suspension of the indicator element within the liquid and a true determination of the direction of liquid flow through visual observation of the indicator element. To accomplish this, at least a portion of the flow channel part of the conduit is made from a transluscent or transparent material so that movement or travel of the indicator element may be visually observed.

Generally, when sufficient irrigating fluid has been received by the intestine to establish evacuation of the fecal matter contained therein, a peristaltic action will develop in the intestine. Initially, as such peristaltic action develops, intestinal fluid pressure will reverse slightly several times. The flow of irrigating liquid from the reservoir due to gravity therefore temporarily stops due to a slight back pressure caused by the initiation of peristaltic action, and then flow resumes to the intestine. However, when sufficient peristaltic action has developed, sufficient intestinal fluid pressure will be created to cause evacuation of the fecal matter and a reverse fluid flow of the irrigating liquid entering the stoma or rectum. Such reversal flow will be sufficient, when the peristaltic action is sufficient, to force the indicator element in the direction of fluid flow. The indicator element is thereby seated or at least positioned in close proximity to one end of the flow channel closest to the irrigating liquid reservoir and farthest from the introduction means.

The user or operator of the subject assembly upon visually observing flow of the indicator element to the extreme opposite end of the flow channel is therefore informed that sufficient irrigating fluid has passed into the intestine and that peristaltic action, sufficient to cause evacuation, has been established.

The invention accordingly comprises the features of construction, combination of elements and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 1 is an isometric view of the assembly including container or irrigating liquid reservoir, elongated conduit and introduction structure such as a stoma cone.

FIG. 2 is an isometric view showing one embodiment of a mounting means for the container.

FIG. 3 is a sectional view along line 3—3 of FIG. 1 showing structural details of an opposite end of a flow channel in the conduit.

FIG. 4 is a sectional view along line 4—4 of FIG. 1 further showing an end of a flow regulating structure for regulating liquid flow through the conduit.

FIG. 5 is a front plan view of a storage or packaging facility wherein the conduit and indicator element is maintained in a liquid environment prior to use.

FIG. 6 is a sectional view along line 6—6 of FIG. 1 showing the indicator element.

DETAILED DESCRIPTION OF THE PREFERRED EMBODIMENT

With reference to FIGS. 1 through 5, the present invention comprises an intestinal irrigating assembly and includes a container generally indicated as 10 formed of lightweight material, such as plastic, and, in one embodiment, may be collapsible for reasons of easy storage and packaging. The container 10 is dimensioned and configured to hold a quantity of irrigating liquid 12 such as water or the like which may contain a softening agent as set forth herein. The container 10 therefore serves as a reservoir of irrigating liquid 12 which passes into an elongated conduit 14 by means of a connector nozzle or like adaptor structure as at 16. The conduit 14 is preferably made of a lightweight plastic material and is at least partially foldable upon itself (see FIG. 5) again for purposes of easy storage and packaging. The elongated conduit depends substantially vertically from the container 12 and is hollow along its length on the interior thereof for the purpose of defining a path of fluid flow of the irrigating liquid 12 as it passes on the container or reservoir 10 along the entire length of the conduit 14 and out of a distal end 14'. The distal end 14' is connected to an introduction means generally indicated as 18 and, in the embodiment shown in FIG. 1, is in the form of a stoma cone 20 structured to be inserted into the opening of the body including the rectum and/or stoma which may be surgically formed. Accordingly, interconnection of the conduit 14 at its opposite ends 14' and 14" to the introduction means 18 and container 10 respectively creates a confined path of fluid flow of the irrigating fluid 12 as it travels, due to gravity, from the container to the interior of the intestine (not shown) exiting from the end or extremity 14'.

As set forth above, the indication of peristaltic action in the intestine will be first indicated by at least one or probably successive "waves or fluctuations" creating back pressure and will in and of itself initially cease fluid flow of the irrigating liquid 12 into the intestine. A backflow will occur which will be clearly indicated by the travel of an indicating element 20 along the length of the conduit 14 and more specifically between opposite ends 22 and 24 of a flow channel portion 24 defined between the opposite ends 22 and 24.

With refernce to FIG. 3, the opposite ends 22 and 24 are crimped as at 25 or otherwise structured to reduce the size of the cross section in order to prevent passage therebeyond of the indicator element 20 while allowing the irrigating liquid to pass through as provided by reduced size apertures 28.

With regard to FIG. 1, indicator element 20 is specifically structured so as to be "suspended" within the irrigating fluid 12 which passes through the flow channel 23. More specifically, the indicator element 20 is specifically structured to have a specific gravity only minimally greater than that of the irrigating liquid 12 (water) passing through the flow channel 23. In a preferred embodiment shown in FIG. 6, the indicator element 20 is preferably formed from a fibrous, absorbable material, such as cotton, 30, surrounding and extending outwardly from a central core 32 which may not necessarily be water absorbable. However, the fibrous material 30 is in fact water absorbable and, if stored or placed in a liquid medium will in fact become saturated. In such saturated state, the indicator element is structured to be "suspendable" in the irrigating liquid 12 and therefore readily travel with the irrigating fluid in its direction of travel. As set forth above, due to the reduced size of the ends 22 and 24, the indicator element may only travel along the flow channel 23 but in the same direction of travel of the irrigating liquid. Accordingly, when the irrigating liquid 12 is passing from the reservoir defined by container 10 to the intestine as it exits from end 14' and the stome cone 21, the direction of travel of the indicator element will pass towards and eventually be stopped against end 22. This is an indication to the observer or user of the assembly that irrigating liquid is still passing into the intestine.

However, upon a first indication of peristaltic action being established in the intestine, a backflow or fluctuating movement of the indicator element 20 will begin and will be indicated by a beginning of travel of the indicator element 20 towards the opposite end 24. However, when the indicator element 20 reaches the opposite end 24, it is a clear indication to the operator or user of the subject assembly that sufficient peristaltic action has been established in the intestine to provide for evacuation of the fecal matter. This will prevent over-irrigation or the supplying of too much irrigating liquid to the intestine even to the point of doing damage to the patient.

Clear indication of the indicating element 20 is provided due to at least a portion or all of the conduit 14 and especially the conduit portion defining the flow channel 23 being made of a transparent or transclucent material so as to allow visual observation of the indicator element 20.

In operation, the user or operator of the subject assembly will cause a ceasing of irrigating fluid into the intestine or from the reservoir 10 to the stoma cone 21 by a flow regulating device indicated generally as 38 in FIG. 4. Such flow regulating device 38 is of conventional design and includes a single plate or planar element 40 having a portion 42 of reduced diameter or transverse dimension size such that when the conduit 14 is placed in the portin 42, flow will cease due to the fact that the conduit 14 will in fact be crimped to a closed position. The position represented in solid lines in FIG. 4 shows a clear flow of irrigating liquid 12 through the conduit 14.

With regard to FIG. 5, the conduit 14 and indicator element 20 is shown stored in a package like structure 31 and submerged in a liquid material such as water 12'. Such storage of the indicator element 20, at least for a minimal period of approximately one hour is required in order to accomplish the above noted saturation of the material 30 in order for the indicator element to be properly suspended in the irrigating liquid 12 within the conduit. Accordingly, by virtue of this structure of the indicating element 20, the flow channel portion 23 of conduit 14 does not have to be maintained in a true horizontal position but may be naturally disposed in a depending or even substantially vertical orientation as shown in FIG. 1.

Other structural features of the present invention include a mounting means secured to one portion of the container 10 (see FIG. 2) wherein the mounting means includes an adhesive structure 46 covering one surface portion of container 10 and initially covered by a removably secured strip 42. The adhesive element or structure 46 may be applied directly to a wall surface or other supporting surface in a manner which serves to position the container 10 in a location which is above the point of application of the irrigating liquid as at end 14' of conduit 14 or the location of introduction of the stoma cone 21. In a preferred location, the container 10 is generally positioned at eye level so as to allow clear observation of the indicator element 20 and its flow through the flow channel 23. Another embodiment of the mounting means may include a ring element 44 which may be mounted on a top portion of the containe as at 10' and may serve to support the container 10 on a supporting hook or like element when it is not practical to use the adhesive element 46.

It is therefore to be understood that the following claims are intended to cover all of the generic and specific features of the invention herein described, and all statements of the scope of the invention which as a matter of language, might be said to fall therebetween.

Now that the invention has been described,

What is claimed is:

1. An irrigation assembly of the type designed for the flushing of fecal matter from an intestine, said assembly comprising:
    (a) a container structure to contain irrigating liquid therein and thereby define a reservoir for storage of irrigating liquid prior to and during an irrigating process,
    (b) introduction means for introducing the irrigating liquid into the intestine being flushed,
    (c) a conduit having an elongated configuration and a hollow interior extending along the length thereof, said conduit attached at its opposite ends to said container and said introduction means respectively,
    (d) said conduit interconnected in fluid communication with and between said container and said introduction means and structured to define a path of fluid fow of said irrigating liquid between said reservoir and an intestine to which that introduction means is secured,
    (e) an indicator element dimensioned and configured to pass along a flow path on the interior of said conduit, said flow path defined by a predetermined length of said conduit spaced from said opposite end thereof,
    (f) said indicator element structured to have a specific gravity substantially equal to water and be substantially suspended therein when said conduit is disposed in a substantially upright orientation, (g) said indicator element further structured and disposed to travel in a direction of liquid flow along said flow path to a first end thereof as said irrigating liquid passes from said reservoir to said introduction means, (h) said indicator element further structured to travel from said first end of said flow path to a second end thereof upon reverse flow of irrigating liquid along said path of fluid flow caused by establishment of peristaltic action within the intestine being flushed, (i) said conduit being constructed along at least a portion of said flow path for monitoring of travel of said indicator element along the length of said flow path between said first and second end thereof, (j) said first and said second ends of said flow path each comprising flow restricting structures formed on said conduit and dimensioned to prevent passage of said indicator element therebeyond, (k) flow control means attached to said conduit and disposed and structured for controlling flow of said irrigating liquid from said reservoir to said introduction means and the intestine being flushed, and (l) said flow control means activated to stop flow to the intestine upon travel of said indicator element to said second end of said flow path.

2. An assembly as in claim 1 wherein said container is mounted on a supporting surface in a vertically higher position than said introduction means at its point of application to the intestine.

3. An assembly as in claim 2 wherein said conduit is disposed in a downwardly depending position from said container to said introduction means and said conduit and said indicator element therein disposed in a substantially vertical orientation.

4. An assembly as in claim 3 further comprising mounting means secured to said container for attachment thereof to the support surface, said mounting means comprising a mounting element structured for removable engagement with the mounting surface.

5. An assembly as in claim 4 wherein said mounting element comprises an adhesive structure disposed on an exposed surface of said container and oriented for removable securement to the supporting surface.

6. An assembly as in claim 1 wherein said container and said conduit are formed from a flexible material capable of being at least partially oriented in a collapsed position for packaging and storage.

7. An assembly as in claim 6 wherein said containr and conduit are formed of a lightweight, plastic material designed for disposal along with said indicator element after use thereof.

8. An assembly as in claim 1 wherein said indicator element is at least partially constructed from a fibrous, liquid absorbable material, said indicator element stored in a liquid for a period of time sufficient to accomplish saturation of said liquid absorable material prior to use.

9. An assembly as in claim 8 wherein said indicator element comprises an elongated configuration defined by an elongated core disposed in colinear relation to a central longitudinal axis of said indicator element, said liquid absorbable material disposed in surrounding outwardly extending relation to said core and attached thereto.

10. An assembly as in claim 9 wherein said core is formed from a material being non-absorbable to liquid and said liquid absorbable material comprising a plurality of cotton fibers.

11. An assembly as in claim 1 wherein said conduit comprises a transparent portion extending along at least a portion of said flow path and disposed and structured for visual observation of said indicator element and the travel thereof along the length of said flow path between said first and said second end thereof.

* * * * *